(12) United States Patent
Uchiyama et al.

(10) Patent No.: US 7,939,060 B2
(45) Date of Patent: *May 10, 2011

(54) ISOFLAVONE-CONTAINING COMPOSITION

(75) Inventors: Shigeto Uchiyama, Saga (JP); Tomomi Ueno, Kurume (JP); Megumi Kumemura, Kurume (JP); Kiyoko Imaizumi, Kurume (JP); Kyosuke Masaki, Kurume (JP); Seiichi Shimizu, Tosu (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 543 days.

This patent is subject to a terminal disclaimer.

(21) Appl. No.: 11/971,458

(22) Filed: Jan. 9, 2008

(65) Prior Publication Data

US 2008/0131412 A1 Jun. 5, 2008

Related U.S. Application Data

(62) Division of application No. 10/752,674, filed on Jan. 8, 2004, now Pat. No. 7,345,089, which is a division of application No. 09/485,320, filed as application No. PCT/JP98/03460 on Aug. 4, 1998, now Pat. No. 6,716,424.

(30) Foreign Application Priority Data

Aug. 8, 1997 (JP) .................................. 1997-214604

(51) Int. Cl.
*A61K 35/74* (2006.01)
*C12P 17/02* (2006.01)

(52) U.S. Cl. .................... 424/93.3; 424/93.44; 424/725; 424/116; 435/119; 435/252.1; 514/456

(58) Field of Classification Search .......................... None
See application file for complete search history.

(56) References Cited

U.S. PATENT DOCUMENTS

| | | | |
|---|---|---|---|
| 4,268,434 A | 5/1981 | Higerd et al. | |
| 5,229,113 A | 7/1993 | Kosslak et al. | |
| 5,902,578 A | 5/1999 | Halpin-Dohnalek et al. | |

FOREIGN PATENT DOCUMENTS

| | | |
|---|---|---|
| JP | 50/035393 | 4/1975 |
| JP | 59-199630 | 11/1984 |
| JP | 60/199396 | 10/1985 |
| JP | 01/268640 | 10/1989 |
| JP | 02/084142 | 3/1990 |
| JP | 4-356479 | 12/1992 |
| JP | 5-176711 | 7/1993 |
| JP | 05/328929 | 12/1993 |
| JP | 9-157268 | 6/1997 |
| JP | 09/237647 | 9/1997 |
| JP | 409238647 | 9/1997 |
| WO | WO 94/23716 | 10/1994 |

OTHER PUBLICATIONS

Chang-Yu-Chen et al, J. of Natural Products, 58(12): 1892-1896 (1995).
The Merck Index, p. 618 (1996).
Balows et al, The Prokaryotes, IV:3597-3598 (1991).
ATCC Catalogue of Bacteria, p. 344 (1996).
Carlsson et al, J. of Clin. Microbio., US, 6(3): 280-284 (1997).
Tang, B. Y. and N. R. Adams. 1980. Effect of Equol on Oestrogen Receptors and on Synthesis of DNA and Protein in the Immature Rat Uterus. Journal of Endocrinology 85: 291-297.
Hutchins et al., J. of American Dietetic Assoc., 1996, vol. 95, No. 5, pp. 545-551.
http://www.innerself.com/Health/urine.htm, (from Urine Therapy: Nature's Elixir for Good Health 1997) accessed Nov. 9, 2006.
Axelson, M., D. N. Kirk, R. D. Farrant, G. Cooley, A. M. Lawson, and K. D. R. Setchell. 1982. The identification of the weak oestrogen equol [7-hydroxy-3-(4'-hydroxyphenyl)chroman] in human urine. Biochemical Journal 201: 353-357.
Chang Yu-Chen et al: "Metabolites of Daidzein and Genistein and Their Biological Activities", Journal of Natural Products (Lloydia), vol. 58, No. 12, Dec. 1995, pp. 1901-1905, XP009094574.
An extended European Search Report dated Jan. 25, 2008.
Setchell, DKR et al: "Nosteroidal Estrogens of Dietary Origin: Possible Roles in Hormone-Dependent Disease", The American Journal of Clinical Nutrition, vol. 40, Sep. 1984, pp. 569-578.

*Primary Examiner* — Irene Marx
(74) *Attorney, Agent, or Firm* — Sughrue Mion, PLLC

(57) ABSTRACT

This invention provides a composition comprising a daidzein-containing substrate and a strain of micro-organism capable of metabolizing daidzein to equol as essential ingredients. This composition is effective in the prevention and alleviation of unidentified clinical syndrome inclusive of menopausal syndrome in middle-aged to elderly women for which no effective means of prevention or alleviation has heretofore been available.

4 Claims, No Drawings

ISOFLAVONE-CONTAINING COMPOSITION

This is a divisional of application Ser. No. 10/752,674 filed Jan. 8, 2004, now U.S. Pat. No. 7,345,089 which is a divisional of application Ser. No. 09/485,320 filed Feb. 8, 2000 (now U.S. Pat. No. 6,716,424), which in turn is a §371 National Stage entry of PCT/JP98/03460, filed Aug. 4, 1998. The entire disclosure of the prior applications, application Ser. Nos. 10/752,674 and 09/485,320 and PCT/JP98/03460, is hereby incorporated by reference.

TECHNICAL FIELD

The present invention relates to an isoflavone-containing composition and more particularly to a novel composition either comprising a daidzein-containing substance and a strain of microorganism capable of metabolizing daidzein to equol or comprising equol obtained by causing said strain of microorganism to act upon said daidzein-containing substance, which composition is useful for the prevention and alleviation of unidentified clinical syndrome and conditions associated with the menopause in middle-aged to elderly women.

BACKGROUND ART

The documented collaborative research of National Cancer Center of Japan and Helsinki University (Finland) attributes the low incidence of gender-specific neoplastic diseases such as carcinoma of the prostate in men and carcinoma of the breast or ovary in women among the Japanese as compared with the European and American people to the greater intake by the Japanese of soybean-derived foods containing various isoflavonoids and the consequent well-coordinated balance of hormones (H. Adlercreutz, et al., (1992) Lancet, 339, 1233; H. Adlercreutz, et al., (1992) Lancet, 342, 1209-1210).

Recently, there has been a mounting interest in the fact that isoflavonoids have estrogen (female hormone)-like activity (A. Molteni, et al., (1995) J. Nutr., 125, 751S-756S), and it has been reported that these compounds are effective in osteoporosis which develops after the menopause when estrogen secretions have subsided or ceased (D. Agnusdei, et al., (1995) Bone and Mineral, 19 (Supple), S43-S48) as well as in menopausal syndrome (D. D. Baird, et al., (1995) J. Clin. Endocrinol, Metab., 80, 1685-1690; A. L. Murkies, et al., (1995) Maturitas., 21, 195-198).

According to the result of a survey undertaken by Margaret Lock (M. Lock, et al., (1988) Maturitas., 10, 317-332), the incidence of menopausal syndrome among the Japanese women is extremely low as compared with the Canadian counterparts. Based on the report, H. Adlercreutz and coworkers conjecture that the Japanese women ingest large amounts of processed soybean foods such as tofu, miso, soy sauce, etc. and, hence, the plant estrogens (isoflavonoids) occurring in those foods are responsible for the low incidence of menopausal syndrome. Comparing the urinary excretions (24-hour urine) which are known to reflect the amount of absorption of isoflavonoids actually ingested, the same authors further report that compared with the Western women, the urinary excretions in the Japanese women are tens of times as high (C. Herman, et al., (1995), J. Nutr., 125, 757S-770S).

It is, thus, considered that the intake of isoflavonoids such as daidzein, genistein, daidzin, genistin, etc. is effective for the alleviation and prevention of postmenopausal osteoporosis and menopausal syndrome. Particularly, the postmenopausal life expectancy in women has reportedly increased to more than 30 years owing to the recent trend toward longevity and the alleviation and prevention of various diseases and symptoms which may develop after the menopause have important meanings in that they would lead to improvements in quality of life (QOL).

However, the above report, i.e. the survey report on the amount of intake of isoflavonoids and the urinary excretions of isoflavonoids in the middle-aged to elderly women in Japan reflects the results generated in a limited rural area and no substantive information is available. Moreover, the correlation between the frequency of menopausal syndrome and the amount of intake of isoflavonoids has not been squarely analyzed and revealed.

Therefore, the object of the present invention is to provide a novel composition which is effective for the prevention and alleviation of the so-called unidentified clinical syndrome in middle-aged to elderly women, inclusive of menopausal syndrome, for which no effective means of prevention or alleviation has been available.

To accomplish the above object, the inventors first conducted a dietary survey, determination of urinary excretions of isoflavonoids, and a questionnaire survey about menopausal syndrome (unidentified clinical syndrome) in perimenopausal women in a broad geographical area including urban communities.

According to the results of the above investigation conducted in 116 women aged between 40 and 60 who belonged to Fukuoka Dietitian Association, the average amounts of intake of isoflavonoids were 9 mg/day for daidzein and 13 mg/day for genistein. The average urinary excretions of isoflavonoids were 19.6 μmol/day for daidzein and 10.0 μmol/day for genistein, and the average excretions of equol, a metabolite of daidzein, was 11.9 μmol/day (mean of subjects in whom it was detected). Incidentally, although daidzein and genistein were detected in all the subjects, equol was detected only in 46 (51.6%) of the 95 subjects.

Furthermore, women with paramenia and those within 5 years of the menopause being taken together as menopausal subjects, a questionnaire survey was conducted using 17 items which are in routine use in the diagnosis of menopausal syndrome [17 items as a modification of Kupperman menopausal index (Kupperman H. S., et al., (1953), J. Clin. Endocrinol. Metabol., 13, 688-703), i.e. 1. hot flushes, 2. perspiration, 3. local sensation of cold, 4. shortness of breath, 5. numbness of limbs, 6. hypesthesia, 7. difficulty in falling asleep, 8. fitful sleep, 9. irritability, 10. nervousness, 11. melancholy, 12. vertigo, nausea, 13. weakness (fatigue), 14. stiff shoulders, pain in joints, muscular pain, 15. headache, 16. palpitation, 17. tingling sensation] and the simplified menopausal index (SMI) was calculated. With subjects with SMI values not less than 20 being taken as a group of high climacteric symptoms and those with SMI values not greater than 19 as a group of low climacteric symptoms, the amount of intake of isoflavonoids and the urinary excretion of isoflavonoids were respectively compared between the groups.

As a result, whereas no intergroup difference was found in the amount of intake of daidzein, the amount of intake of genistein tended to be lower in the group of high climacteric symptoms at p=0.0643. With regard to the urinary excretions of isoflavonoids, no intergroup difference was found whether for daidzein or for genistein but the excretions of equal were significantly low (p<0.01) in the group of high climacteric symptoms.

From the above results, the inventors found that unidentified clinical symptoms in menopausal women are more closely related to the amount of intake of genistein and the urinary excretion of equal, among various isoflavonoids.

In the past the relationship of the amounts of intake and urinary excretion of isoflavonoids as a whole to their physiological effect has been discussed without regard to specific kinds of isoflavonoids such as daidzein and genistein but the results of the survey conducted by the inventors in the Japanese middle-aged and elderly women made it clear that not only the amounts of intake and urinary excretion of isoflavonoids in general but also the amount of intake of genistein and the urinary excretion of equol, particularly the rate of metabolic conversion of daidzein to equol, are closely related to unidentified clinical climacteric symptoms in menopausal women.

In another study undertaken by the inventors in healthy adult volunteers (25-33 years of age), it was found that the urinary excretions of isoflavonoids (daidzein and genistein) after single ingestion of soy milk, a representative isoflavonoid-containing food, are increased in a dose-related fashion but in subjects who showed no urinary excretion of equol, equol was not detected in the urine even when the amount of intake of soy milk was increased two-fold, indicating the existence of individual difference in the metabolic pathway from daidzein to equol.

It is known that equol, which is a metabolite of daidzein, is not detected in isoflavonoid-containing foods such as processed soybean products nor is it taken into the body from foods in ordinary diets (K. Reinli, et al., (1996), Nutr. Cancer, 26, 123-148).

Based on the above findings the inventors did further research and, as a result, succeeded in the development of a novel composition which comprises a strain of microorganism having the ability (metabolic activity) to elaborate equol from daidzein and either daidzein or a suitable substance containing daidzein in combination, and a novel composition which comprises equol obtained by causing said strain of microorganism to assimilate daidzein. The inventors then discovered that the intake of whichever of the above compositions is effective in the prevention and alleviation of unidentified clinical syndrome in middle-aged and older women and have accordingly developed the instant invention.

DISCLOSURE OF INVENTION

The present invention in a first aspect provides a composition, in the form of a food or a pharmaceutical product, which comprises a daidzein-containing substance and a strain of microorganism capable of metabolizing daidzein to equol as essential ingredients (which composition will hereinafter be referred to as "isoflavone-containing composition").

The present invention in a second aspect provides a composition, in the form of a food or a pharmaceutical product, which comprises equol which is obtained by causing a strain of microorganism capable of metabolizing daidzein to equol to act upon a daidzein-containing substance (which composition will hereinafter be referred to as "equol-containing composition").

The present invention further provides said isoflavone-containing composition and equol-containing composition wherein the strain of microorganism capable of metabolizing daidzein to equol is at least one member selected from the group consisting of *Bacteroides ovatus, Streptococcus intermedius* and *Streptococcus constellatus* and more particularly said isoflavone-containing composition and equol-containing composition wherein said strain of microorganism is at least one member selected from the group consisting of *Bacteroides* E-23-15, which has been deposited as FERM BP-6435, *Streptococcus* E-23-17, which has been deposited as FERM BP-6436, and *Streptococcus* A6G-225, which has been deposited as FERM BP-6437.

The present invention further provides said isoflavone-containing composition and equol-containing composition which further contain at least one ingredient that favors the maintenance and growth of said strain of microorganism, for example at least one substance selected from the group consisting of galactosylsucrose, soybean-oligosaccharide, lactulose, lactitol and fructo-oligosaccharide.

The present invention further provides said isoflavone-containing composition and equol-containing composition wherein said daidzein-containing substance further contains at least one member selected from the group consisting of genistein, daidzin and genistin, more preferably soya isoflavone.

The present invention further provides said isoflavone-containing composition and equol-containing composition for the prevention and treatment of unidentified clinical syndrome in middle-aged to elderly women, inclusive of menopausal syndrome.

The present invention further provides said isoflavone-containing composition and equol-containing composition in the form of a food which is selected from the group consisting of drinks, dairy products, fermented milk, bars, granules, powders, capsules and tablets.

The present invention further provides said isoflavone-containing composition and equol-containing composition in the form of a pharmaceutical product which is selected from the group consisting of aqueous solutions, emulsions, granules, powders, capsules and tablets.

The present invention in a further aspect provides a method for prevention and treatment of unidentified clinical syndrome or menopausal syndrome in middle-aged to elderly women which comprises administering an effective amount of said isoflavone-containing composition or equol-containing composition to a middle-aged or elderly woman in whom said prevention or treatment are needed.

The present invention further provides the use of a microorganism capable of utilizing a daidzein-containing substrate or daidzein to produce equol for the production of said isoflavone-containing composition and equol-containing composition which are effective for the prevention and treatment of unidentified clinical syndrome or menopausal syndrome in middle-aged to elderly women.

The present invention further provides a method of producing equol which comprises causing a strain of microorganism capable of metabolizing daidzein to equol to act upon daidzein.

The present invention further provides a strain of microorganism selected from the group consisting of *Bacteroides* E-23-15, which has been deposited as FERM BP-6435, *Streptococcus* E-23-17, which has been deposited as FERM BP-6436, and *Streptococcus* A6G-225, which has been deposited as FERM BP-6437.

The isoflavone-containing composition of the invention is now described in detail.

In the isoflavone-containing composition of the invention, a daidzein-containing substance is used as one of its essential ingredients. This daidzein-containing substance includes not only daidzein as such but also daidzin which is a glycoside of daidzein and a variety of substances containing daidzein and/or daidzin. The daidzein present itself chiefly in soybean, kudzu and the like raw foods, their processed products such as tofu, aburage, soy milk, etc. and their fermentation products such as natto, soy sauce, miso, tempeh, etc. In the present invention, any of such raw foods, processed products and fermentation products can be used as said daidzein-containing substance. Particularly, the substances contain not only daidzein but also other isoflavonoids having estrogen-like activity, such as genistein, daidzin, genistin, etc., biochain A and formonetin which is a partially methylated precusor of genistein and daidzein, respectively, etc. and can be used with advantage for the purpose of the invention.

The daidzein-containing substance which is preferred for the practice of the present invention further includes soya isoflavone derived from soybeans, for example commercial products such as "Fujiflavone (trade name) P10" from Fujicco, and isoflavonoids derived from plants such as red clove, alphalpha, etc.

In the isoflavone-containing composition of the invention, a strain of microorganism having an ability (metabolic activity) to produce equol from daidzein is used as the other essential ingredient. The microorganism includes those belonging to *Bacteroides ovatus, Streptococcus intermedius,* and *Streptococcus constellatus*. Particularly preferred among such microorganisms are *Bacteroides* E-23-15 (FERM BP-6435), *Streptococcus* E-23-17 (FERM BP-6436) and *Streptococcus* A6G-225 (FERM BP-6437), all of which were isolated from human stools and deposited for accession by the inventors.

The bacteriological characteristics of those strains of microorganisms are now described in detail.

(1) *Bacteroides* E-23-15, FERM BP-6435

I. Cultural Characters

When cultured anaerobically using an anaerobic jar stuffed with steel wool at 37° C. for 48 hours, this strain gives good to moderate growth on Eggerth-Gagnon (EG) agar, Blood Liver (BL) agar, or Gifu Anaerobic Medium (GAM). The colonies are circular, protuberant in a convex manner, with both the surface and peripheral edges being glabrous to slightly coarse. The colony color is grayish white on EG agar or grayish brown on BL agar. Morphologically it is a gram-negative rod and shows polymorphism ranging from coccobacillus, single rod, elongated rod, etc., but the cells occur singly and not in chains. No sporogenesis is found.

II. Physiological Characteristics
(1) Optimum temperature for growth: 37° C.
(2) Optimum pH for growth: 7.0
(3) Liquefaction of gelatin: +
(4) Hydrolysis of soluble starch: +
(5) Hydrolysis of esculin: +
(6) Indole production: –
(7) Urease: –
(8) Catalase: –
(9) Assimilation of carbon sources:
L-arabinose +
D-xylose +
D-glucose +
Sucrose +
L-Rhamnose +
D-Raffinose +
D-Mannitol +
Indole +
Lactose +
Maltose +
Salicin +
Gelatin +
Glycerin +
D-cellobiose +
D-mannose +
D-melezitose +
D-sorbitol +
D-trehalose +

(10) Organic acid composition after utilization of peptone or glucose:

Using PYF (peptone-yeast extract-Fildes) medium (containing about 5% of peptone), which is utilized in sugar fermentation test, and PYF medium supplemented with 0.5% final concentration of glucose, the strain was cultured anaerobically at 37° C. for 72 hours and the organic acids in the resulting culture were assayed by HPLC. The results (unit: mM) are shown below.

| Organic acid | PYF culture | Glucose-PYF Culture |
|---|---|---|
| Maleic acid | 0.02 | 1.19 |
| Succinic acid | 0.01 | 3.20 |
| Lactic acid | 0.01 | 4.94 |
| Formic acid | 0.03 | 0.66 |
| Acetic acid | 0.29 | 2.62 |
| Pyroglutamic acid | 0.01 | nd |
| Propionic acid | nd | nd |
| i-Butyric acid | 1.71 | 0.23 |
| n-Butyric acid | 0.36 | nd |
| i-Valeric acid | nd | 0.19 |
| n-Valeric acid | nd | nd | nd = not detected

The above morphological and biochemical characteristics, sugar fermentation test and organic acid production spectrum suggested that this strain was either of the gram-negative rods *Bacteroides ovatus* and *Bacteroides uniformis* but was decided to be a microorganism belonging to *Bacteroides ovatus* in view of its ability to utilize rhamnose. Accordingly this strain was named *Bacteroides* E-23-15 and deposited with National Institute of Bioscience and Human Technology (NIBH, Higashi 1-1-3, Tsukuba-shi, Ibaraki, Japan) as of Jul. 7, 1997 under the accession number of FERM P-16312. This deposit was converted to a Budapest deposit on Jul. 22, 1998 and assigned the accession number of FERM BP-6435.

(2) *Streptococcus* E-23-17 (FERM BP-6436)

I. Cultural Characteristics

When cultured anaerobically in an anaerobic jar stuffed with steel wool at 37° C. for 48 hours, this strain gives good to moderate growth on EG agar, BL agar or GAM. The colonies are circular and conical to protuberant in a centrally convex fashion, and have a ground glass-like to granular texture with a smooth or slightly coarse edge. The colonies on EG agar are transparent to grayish brown. Morphologically it is a gram-positive coccus, ellipsoidal or with slightly pointed ends. The cells occur singly or are diplococcal, forming irregular masses. No chain is formed. The strain is not sporogenic.

II. Physiological Characteristics
(1) Optimum temperature for growth: 37° C.
(2) Optimum pH for growth: 7.0
(3) Liquefaction of gelatin: –
(4) Hydrolysis of soluble starch: –
(5) Hydrolysis of esculin: +
(6) Indole production: –
(7) Urease: –
(8) Catalase: –
(9) Assimilation of carbon sources:
L-arabinose +
D-xylose –
D-glucose +
Sucrose –
L-Rhamnose +
D-Raffinose –

D-Mannitol +
Indole –
Lactose +
Maltose +
Salicin +
Gelatin –
Glycerin –
D-cellobiose +
D-mannose +
D-melezitose –
D-sorbitol +
D-trehalose +

(10) Organic acid composition after utilization of peptone or glucose:

Using PYF (peptone-yeast extract-Fildes) medium (containing about 5% of peptone), which is utilized in sugar fermentation test, and PYF medium supplemented with 0.5% final concentration of glucose, the strain was cultured anaerobically at 37° C. for 72 hours and the organic acids in the resulting culture were assayed by HPLC. The results (unit: mM) are shown below.

| Organic acid | PYF culture | Glucose-PYF Culture |
| --- | --- | --- |
| Maleic acid | 0.04 | Nd |
| Succinic acid | 2.37 | 0.02 |
| Lactic acid | 0.02 | nd |
| Formic acid | 0.03 | 0.03 |
| Acetic acid | 3.32 | 0.07 |
| Pyroglutamic acid | 0.03 | nd |
| Propionic acid | 3.24 | nd |
| i-Butyric acid | 4.17 | 1.11 |
| n-Butyric acid | nd | nd |
| i-Valeric acid | 4.50 | nd |
| n-Valeric acid | nd | nd | nd = not detected

The above morphological and biochemical characteristics, sugar fermentation test and organic acid production spectrum suggest that this strain belongs to either of the gram-positive cocci *Luminococcus productus* and *Streptococcus constellatus* but the strain differentiates itself from the type culture strain of *Luminococcus productus* in the ability to utilize sucrose, D-xylose and D-raffinose. Therefore, the inventors named the strain *Streptococcus* E-23-17 and deposited it with National Institute of Bioscience and Human Technology (NIBH, Higashi 1-1-3, Tsukuba-shi, Ibaraki, Japan) as of Jul. 7, 1997 under the accession number of FERM P-16313. This deposit was subsequently converted to a Budapest deposit as of Jul. 22, 1998 and assigned with the accession number of FERM BP-6436.

(3) *Streptococcus* A6G-225 (FERM BP-6437)

I. Cultural Characteristics

When cultured anaerobically using an anaerobic jar stuffed with steel wool at 37° C. for 48 hours, this strain shows good to moderate growth on EG agar, BL agar or GAM. The colonies are circular, conical to protuberant in a centrally convex fashion and have ground glass-like to granular texture with a smooth or slightly coarse peripheral edge. The colonies on EG agar are transparent to grayish white. Morphologically it is a gram-positive coccus, ellipsoidal or with slightly pointed ends. The cells occur singly or are diplococcal, forming irregular masses. No chain is formed. No sporogenesis is found, either.

II. Physiological Characteristics (1) Optimum temperature for growth: 37° C.
(2) Optimum pH for growth: 7.0
(3) Liquefaction of gelatin: –
(4) Hydrolysis of soluble starch: –
(5) Hydrolysis of esculin: +
(6) Indole production: –
(7) Urease: –
(8) Catalase: –
(9) Assimilation of carbon sources:
    L-arabinose –
    D-xylose –
    D-glucose +
    Sucrose +
    L-Rhamnose –
    D-Raffinose +
    D-Mannitol –
    Indole –
    Lactose +
    Maltose +
    Salicin +
    Gelatin –
    Glycerin –
    D-cellobiose +
    D-mannose +
    D-melezitose –
    D-sorbitol –
    D-trehalose –

(10) Organic acid composition after utilization of peptone or glucose:

Using PYF (peptone-yeast extract-Fildes) medium (containing about 5% of peptone), which is utilized in sugar fermentation test, and PYF medium supplemented with 0.5% final concentration of glucose, the strain was cultured anaerobically at 37° C. for 72 hours and the organic acids in the resulting culture were assayed by HPLC. The results (unit: mM) are shown below.

| Organic acid | PYF culture | Glucose-PYF culture |
| --- | --- | --- |
| Maleic acid | nd | Nd |
| Succinic acid | 0.21 | 0.03 |
| Lactic acid | nd | 35.36 |
| Formic acid | 0.55 | 1.66 |
| Acetic acid | 1.35 | 0.54 |
| Pyroglutamic acid | nd | nd |
| Propionic acid | nd | nd |
| i-Butyric acid | 2.04 | nd |
| n-Butyric acid | nd | nd |
| i-Valeric acid | nd | nd |
| n-Valeric acid | nd | nd | nd = not detected

The above morphological and biochemical characteristics, sugar fermentation test and organic acid production spectrum suggest that this strain belongs to the gram-positive *Streptococcus intermedius* but the strain differentiates itself from the type culture strain of *S. intermedius* in the ability to utilize L-rhamnose and D-trehalose. Therefore, the inventors named the strain *Streptococcus* A6G-225 and deposited it with National Institute of Bioscience and Human Technology (NIBH, Higashi 1-1-3, Tsukuba-shi, Ibaraki, Japan) as of Jul. 7, 1997, with the accession number of FERM P-16314 assigned. This deposit was subsequently converted to a Budapest deposit as of Jul. 22, 1998 and assigned with the accession number of FERM BP-6437.

The above three strains of microorganisms isolated by the inventors have the ability to utilize daidzein to elaborate equol as their most outstanding characteristic. The daidzein includes daidzein as the aglycone of an isoflavone glycoside such as daidzin. Daidzin is utilized by said microorganisms to give daidzein, and equol is then produced from this daidzein.

There has been no report on such a microorganism capable of producing equol. Therefore, the present invention further provides novel strains of microorganisms having the ability to produce equol.

The above strain of microorganism for use as an essential ingredient of the isoflavone-containing composition of the invention may generally be the live microorganism as such. However, it is not limited thereto but includes its culture, a crude or purified product thereof, and their lyophilyzates. Its proportion is not particularly restricted but can be judiciously selected according to the kind of microorganism, among other factors. For example, in the case of *Streptococcus intermedius* in fermented milk, the bacterial count is preferably controlled within the range of about $10^8$ to $10^9$ cells/ml. The bacterial count is determined by inoculating an agar medium with a diluted sample, incubating the inoculated medium anaerobically at 37° C. and counting the colonies formed. In the case of other strains of microorganisms, too, the count determined in the above manner can be used as a rule of thumb.

The isoflavone-containing composition of the invention further preferably contains a nutrient component particularly suited to the maintenance and growth of the particular strain of microorganism. The nutrient component includes various oligosaccharides such as galactosylsucrose, soybean-oligosaccharide, lactulose, lactitol, fructo-oligosaccharide, and galacto-oligo-saccharide. The formulating amount of such nutrients is not particularly restricted but generally is preferably selected from the range of about 1 to 3 weight % based on the total composition of the invention.

The composition of the invention is generally prepared by blending predetermined amounts of said essential ingredients and other optional ingredients and processing the mixture into a suitable food form or pharmaceutical dosage form, such as drinks, dairy products, fermented milk, bars, granules, powders, capsules, tablets, etc. for food use or aqueous solutions, emulsions, granules, powders, capsules, tablets, etc. for pharmaceutical use. The production of such dosage forms can be carried out in the conventional manner. The carrier for use in the manufacture of such dosage forms includes edible carriers and pharmaceutically acceptable excipients and diluents. Particularly in the case of a food form, a palatable and taste-improving carrier is preferred.

The particularly preferable examples of carrier include such masking agents as trehalose (manufactured by Hayashibara), cyclodextrin, Benekote BMI (manufactured by Kao Corporation), etc.

The blending ratio of said daidzein-containing substance, specific strain of microorganism and optional ingredients used for the maintenance and growth of the microorganism is not particularly critical. However, based on 100 g of the composition of the invention, the proportion of the daidzein-containing substance is preferably within the range of about 10-50 mg of daidzein contained therein. On the same basis, the proportion of the microorganism is preferably $10^9$ to $10^{10}$ cells (as viable cells) and that of the oligosaccharide is preferably within the range of about 1-5 g.

Since the isoflavone-containing composition of the invention contains a strain of microorganism (primarily live cells) as mentioned above, the composition preferably should not be subjected to heating and/or pressurization in the course of processing into final products. Therefore, in processing the composition of the invention into such dosage forms as bars, granules, powders, tablets, etc., it is preferable to add the microorganism as lyophilized cells as such or lyophilized cells coated with a suitable coating agent.

The composition of the invention may be optionally supplemented with various other food ingredients having nutritional values or various additives which are conventionally used in the manufacture of pharmaceutical products. The food ingredients mentioned above include calcium, vitamin B, vitamin D, vitamin C, vitamin E and vitamin K (particularly MK-7 (menaquinone-7) derived from *Bacillus natto*). Other examples of the substances that can be added include zinc and selenium.

The resulting isoflavone-containing composition of the invention is useful for the prevention and treatment of unidentified clinical syndrome, postmenopausal osteoporosis and other menopausal syndrome and symptoms in middle-aged and older women. Such prevention and treatment are achieved by administering or ingesting an effective amount of the above composition of the invention to a middle-aged or elderly woman who needs such prevention or treatment. The effective amount of the composition is not particularly restricted insofar as the prevention and treatment of unidentified clinical syndrome, postmenopausal osteoporosis or menopausal syndrome can be achieved with it. In general, the effective amount is preferably such that about 10-50 mg/day of daidzein and at least about 10 mg/day of genistein can be taken.

The equol-containing composition of the invention is now described in detail.

The equol-containing composition of the invention comprises equol obtainable by causing a strain of microorganism capable of utilizing daidzein to produce equol to act upon a daidzein-containing substance.

The strain of microorganism may be the same as that of the above-described isoflavone-containing composition of the invention. The daidzein-containing substance on which said microorganism is caused to act can also be the same as that mentioned for the isoflavone-containing composition of the invention, thus including an isolated and purified form of daidzein, food materials containing it, processed matters or fermentation products thereof, soya isoflavone and isoflavones derived from kudzu, red clove, alphalpha, etc., products containing such isoflavones, for example tofu, soy milk, boiled soybeans, natto, soybean hypocotyl extract, etc.

The equol-containing composition of the invention is very safe because the active ingredient thereof is a native substance as mentioned above. Moreover, since it is prepared by using a microorganism, the composition is not only free from contamination with chemicals and the like contaminants but also advantageous in that it can be obtained in high yield and at low production cost.

The equol-containing composition of the invention can be produced by conventional fermentation technology utilizing said daidzein-containing substance, preferably soya isoflavone or a food material containing it, as the substrate.

More particularly, the technology comprises sterilizing the substrate in solution form, adding the predetermined strain of microorganism thereto, and incubating the mixture at 37° C. either under anaerobic conditions or under aerobic stationary conditions for about 48-96 hours to let fermentation proceed. (Where necessary, a pH control agent, a reducing substance (e.g. yeast extract, vitamin $K_1$) can be added).

Taking *Streptococcus intermedius* as an example, the above cultural process can be more preferably carried out as follows. First, daidzein is dissolved in the range of 0.01-0.5 mg/ml in Modified GAM (Modified Gifu Anaerobic Medium) for culture of anaerobic bacteria. A seed culture prepared by growing the microorganism in Modified GAM for about 14 hours is then inoculated into the above daidzein-containing Modified GAM. The inoculum size may be 1/100 by volume of the medium. The incubated medium is incubated aerobically at 37° C. under stationary conditions for 48-96 hours.

The present invention further provides a method of producing equol utilizing such a strain of microorganism.

In the above fermentation system, there may be incorporated a nutrient which is particularly suited for the maintenance and growth of the microorganism. The nutrient includes oligosaccharides such as galactosyl-sucrose, soybean-oligosaccharide, lactulose, lactitol, fructo-oligosaccharide, and galacto-oligosaccharide. The amount of said nutrient is not particularly restricted but is preferably selected from the range of generally about 1-3 weight % based on the total composition of the invention.

The desired equol-containing culture broth can thus be obtained.

Isolation and purification of equol from the fermentation broth can be carried out in the conventional manner. A typical procedure may comprise adsorbing the fermentation broth on an ion exchange resin (e.g. DIAION HP20, Mitsubishi Kasei Corporation), eluting the objective substance with methanol, and concentrating the active fraction to dryness to provide crude equol.

The equol-containing composition of the invention can be produced, in a suitable food form or pharmaceutical dosage form, by formulating the equol-containing culture broth prepared as above or equol isolated therefrom with other optional food materials.

The food form includes drinks, milk products, fermented milk, bars, granules, powders, capsules, and tablets. The pharmaceutical dosage form includes aqueous solutions, emulsions, granules, powders, capsules and tablets. Those food or pharmaceutical dosage forms can each be manufactured by the established technology. The carrier for use in the manufacture of such forms may be any of edible carriers and pharmaceutically acceptable excipients and diluents. Particularly in the case of foods, the carrier is preferably a palatable, taste-improving carrier.

The amount of equol in the resulting composition of the invention is not particularly restricted but can be determined according to the intended food form or pharmaceutical dosage form. Usually, however, based on 100 g of the total composition, the amount of equol is preferably about 10-50 mg.

The amount of intake of the composition of the invention is not particularly restricted but can be generally selected so that the urinary excretions of equol after ingestion of the composition will not be less than 5 μmole/day.

The equol-containing composition of the invention is useful for the prevention and treatment of unidentified clinical syndrome in middle-aged to elderly women, typically symptoms of postmenopausal osteoporosis and menopausal syndrome.

BEST MODE FOR CARRYING OUT THE INVENTION

For a further detailed description of the invention, examples of preparation of the isoflavone-containing composition and equol-containing composition of the invention and an example of production of equol are presented below. It being to be understood, however, that the scope of the invention is not limited by those examples.

EXAMPLE 1

Preparation of a Drink

The ingredients according to the following recipe were weighed and blended to provide the composition of the invention in the form of a beverage.

Fermentation broth of water-soluble soybean protein

| | |
|---|---|
| Fermentation broth of water-soluble soybean protein | 10 ml |
| Galactosylsucrose (55% content) | 10.0 g |
| Vitamins & minerals | q.s. |
| Flavor | q.s. |
| Water | q.s. |
| Total | 150 ml |

The above fermentation broth of water-soluble soybean protein was prepared by dissolving 2.2 g of water-soluble soybean protein in 10 ml of water; adding $10^8$ cells of *Streptococcus* A6G-225 (FERM BP-6437) thereto, and incubating the mixture at 37° C. for 48 hours.

EXAMPLE 2

Preparation of a Fermented Milk

The ingredients according to the following recipe were weighed and blended to provide the isoflavone-containing composition of the invention in the form of fermented milk.

| | |
|---|---|
| Water-soluble soybean protein | 2.2 g |
| Galactosylsucrose (55% content) | 10.0 g |
| *Streptococcus* A6G-225-fermented milk | 100 ml |
| Vitamins & minerals | q.s. |
| Flavor | q.s. |
| Water | q.s. |
| Total | 50 ml |

The water-soluble soybean protein contained about 3-4% of daidzein (as analyzed by high-performance liquid chromatography; the same applies hereinafter). The *Streptococcus* A6G-225-fermented milk was prepared by adding $10^8$ cells of *Streptococcus* A6G-225 (FERM BP-6437) to 1 liter of milk and incubating the mixture at 37° C. for 24 hours.

EXAMPLE 3

Preparation of a Fermented Soy Milk Lyophilizate

Using 1 ml of a suspension of about $10^7$ cells/ml of *Streptococcus* A6G-225 (FERM BP-6437), 100 g of soy milk was caused to undergo lactic acid fermentation at 37° C. for 24 hours to provide equol. This product was lyophilized. The equol content of this freeze-dried powder was 0.1-0.3 weight %.

The above powder and other ingredients according to the following recipe were weighed and blended to provide the composition of the invention in the form of a fermented soy milk lyophilizate.

| | |
|---|---|
| Fermented soy milk lyophilizate | 2.2 g |
| Excipient | q.s. |
| Vitamins & minerals | q.s. |
| Flavor | q.s. |
| Total | 20 g |

As the excipient, 17 g of corn starch was used.

EXAMPLE 4

Preparation of Powders

The ingredients according to the following recipe were weighed and blended to provide the composition of the invention in powdery form.

| | |
|---|---|
| Crude soya isoflavone powder | 4.1 g |
| Galactosylsucrose (55% content) | 10.0 g |
| *Streptococcus* E-23-17 lyophilizate | 1.0 g |
| Vitamins & minerals | q.s. |
| Flavor | q.s. |
| Total | 20 g |

The *Streptococcus* E-23-17 lyophilizate was prepared by growing Streptococcus E-23-17 (FERM BP-6436) in a suitable liquid growth medium (GAM broth) (37° C., 24-48 hours) and lyophilizing the resulting culture. The bacterial cell content of this freeze-dried powder was $10^9$-$10^{10}$ cells/g.

EXAMPLE 5

Preparation of Granules

The ingredients according to the following recipe were weighed and blended to provide the composition of the invention in granular form.

| | |
|---|---|
| Crude soya isoflavone powder | 4.1 g |
| Galactosylsucrose (55% content) | 10.0 g |
| *Streptococcus* E-23-17 lyophilizate | 1.0 g |
| Sorbitol | q.s. |
| Vitamins & minerals | q.s. |
| Flavor | q.s. |
| Total | 20 g |

As the *Streptococcus* E-23-17 lyophilizate, the same freeze-dried powder as in Example 4 was used.

EXAMPLE 6

Microbial Production of Equol

Using a water-soluble soya isoflavone material ("Fujiflavone P10", Fujicco) as the substrate, 1 ml of a suspension of $10^7$-$10^9$ cells of *Streptococcus* A6G-225 (FERM BP-6437) in GAM for culture of anaerobic bacteria was added to a 2.2% aqueous solution of the above substrate. The mixture was incubated aerobically at 37° C. under stationary conditions for 96 hours and the amount of equol produced in the fermentation broth was measured by HPLC. The concentration of daidzin in the above aqueous solution was 1.083 mg/ml, and the concentration of daidzein was 0.014 mg/ml.

As a result, whereas no equol could be detected in the water-soluble soya isoflavone material, the equol content of the fermentation broth after 96 hours of culture was 613.0±8.7 μg/ml (means of 5 determinations ±S.D.). Neither daidzin nor daidzein was detected in the fermentation broth.

Using a substrate solution containing 0.01 mg/ml of daidzein (manufactured by Funakoshi, purity ≧99%) (5 mg of daidzein suspended in 2 ml of special grade methanol and diluted to 50 ml with BHI (brain heart infusion) medium) in lieu of the above water-soluble soya isoflavone material, equol was produced in otherwise the same manner as above. As a result, the amount of equol in the fermentation broth after 96 hours of culture was 17.9±1.4 μg/ml (mean of 5 determinations ±S.D.).

It is, therefore, clear that by utilizing the microorganism of the invention, equol can be produced from daidzein with good efficiency.

EXAMPLE 7

Preparation of a Drink

| | |
|---|---|
| Equol-containing fermentation broth | 1.55 g |
| Glucose | 5.00 g |
| Citric acid | 0.5 g |
| Vitamins & minerals | q.s. |
| Flavor | q.s. |
| Water | q.s. |
| Total | 200 ml |

In the same manner as Example 6, 1 ml of a suspension of $10^7$-$10^9$ cells of *Streptococcus* A6G-225 (FERM BP-6437) in GAM for culture of anaerobic bacteria was added to a 2.2% aqueous solution of water-soluble soya isoflavone material ("Fujiflavone P10", Fujicco) and the mixture was incubated aerobically at 37° C. under stationary conditions for 96 hours. Using the equol-containing fermentation broth thus obtained and other ingredient according to the above recipe, the composition of the invention in the form of a drink was prepared.

EXAMPLE 8

Preparation of a Bar

| | |
|---|---|
| Equol-containing fermentation broth | 1.55 g |
| Butter | 20.0 g |
| Sugar | 20.0 g |
| Salt | Small amount |
| Egg | ½ |
| Wheat flour | 80.0 g |
| Vitamins & minerals | q.s. |
| Flavor | q.s. |
| Milk | 30.0 g |

Using the equol-containing fermentation broth described in Example 7 in accordance with the above recipe, a dough was prepared, molded into a suitable bar form, and baked in an oven at 170° C. for 15 minutes to provide a cake bar.

EXAMPLE 9

Preparation of a Jelly

| | |
|---|---|
| Equol-containing fermentation broth | 1.55 g |
| Fruit juice | 50.0 g |
| Sugar | 50.0 g |
| Agar | 2.5 g |
| Vitamins & minerals | q.s. |
| Flavor | q.s. |

Using the equol-containing fermentation broth described in Example 7 in accordance with the above recipe, the respective ingredients were heated up to 90° C. with constant stirring to dissolve the agar and the whole amount was poured into a suitable cup and cooled for gelation at 5-10° C. to provide the composition of the invention in the form of a jelly.

INDUSTRIAL APPLICABILITY

The composition of the invention, when caused to be ingested or administered in the form of a food or a pharmaceutical product, proves useful for the prevention and alleviation of unidentified clinical syndrome or menopausal syndrome in middle-aged to elderly women.

The invention claimed is:

1. An equol-containing composition which is obtained by incubating at least one strain selected from the group consisting of *Bacteroides* E-23-15, which has been deposited as FERM BP-6435, *Streptococcus* E-23-17, which has been deposited as FERM BP-6436, and *Streptococcus* A6G-225, which has been deposited as FERM BP-6437, with a daidzein-containing substance, which is in a pharmaceutical dosage form.

2. The composition according to claim 1 wherein the pharmaceutical dosage form is selected from the group consisting of aqueous solutions, emulsions, granules, powders, capsules and tablets.

3. A method for producing an equol-containing composition, comprising incubating at least one strain selected from the group consisting of *Bacteroides* E-23-15, which has been deposited as FERM BP-6435, *Streptococcus* E-23-17, which has been deposited as FERM BP-6436, and *Streptococcus* A6G-225, which has been deposited as FERM BP-6437, with a daidzein-containing substance, wherein the composition is in a pharmaceutical dosage form.

4. The method according to claim 3, wherein the pharmaceutical dosage form is selected from the group consisting of aqueous solutions, emulsions, granules, powders, capsules and tablets.

* * * * *